US012755811B1

(12) United States Patent
Willson et al.

(10) Patent No.: US 12,755,811 B1
(45) Date of Patent: Oct. 6, 2026

(54) MAINTAINING HIERARCHICAL REPRESENTATION OF A PROTEIN COMPLEX

(71) Applicant: Benchling, Inc., San Francisco, CA (US)

(72) Inventors: Henry Marfleet Willson, New York, NY (US); Katherine Christiansen-Salameh, San Francisco, CA (US); Hailey Motooka, San Francisco, CA (US); Madison Fletcher, San Francisco, CA (US); Lily Helfrich, Oakland, CA (US)

(73) Assignee: Benchling, Inc., San Francisco, CA (US)

( * ) Notice: Subject to any disclaimer, the term of this patent is extended or adjusted under 35 U.S.C. 154(b) by 0 days.

(21) Appl. No.: 19/358,266

(22) Filed: Oct. 14, 2025

(51) Int. Cl.
*G06F 16/00* (2019.01)
*G06F 16/25* (2019.01)
(Continued)

(52) U.S. Cl.
CPC ........... *G16B 15/00* (2019.02); *G06F 16/258* (2019.01); *G06F 16/26* (2019.01); *G16B 45/00* (2019.02)

(58) Field of Classification Search
CPC ...... G06F 16/258; G06F 16/535; G06F 16/54; G06F 16/94; G06F 18/21375; G06F 16/2471; G06F 40/137; G06F 40/143; G06F 40/18; G06N 3/04; G06N 3/0455; G06N 3/0464; G06N 3/09; G06N 5/04; G06T 15/205; G06T 17/00; G16B 15/00; G16B 15/20; G16B 15/30; G16B 30/00; G16B 30/10; G16B 30/20; G16B 40/20; G16B 5/00; G16B 5/20; G16B 50/40;
(Continued)

(56) References Cited

U.S. PATENT DOCUMENTS

| | | | | |
|---|---|---|---|---|
| 5,418,944 | A * | 5/1995 | DiPace | G16C 20/40 |
| 2004/0203134 | A1* | 10/2004 | Pyntikov | C12P 21/06 435/252.1 |

(Continued)

OTHER PUBLICATIONS

Bornberg-Bauer et al., "Conceptual data modelling for bioinformatics," Briefings in Bioinformatics, Jun. 2002, 3(2):166-180.

(Continued)

*Primary Examiner* — Shyue Jiunn Hwa
(74) *Attorney, Agent, or Firm* — Fish & Richardson P.C.

(57) ABSTRACT

Methods, systems, and apparatus, including computer programs encoded on a computer storage medium, for maintaining data of a hierarchical representation of a protein complex that includes components and automatically generating missing component data of the hierarchical representation of the protein complex. By storing format templates that define structural constraints and hierarchical relationships between components of a protein complex, the described techniques enable standardized and modular representations that reduce data redundancy and improve consistency across protein designs. By automatically generating missing component data using biological transformations, the system improves data integrity, reduces manual errors, and supports scalable protein design and production.

20 Claims, 8 Drawing Sheets

(51) Int. Cl.
*G06F 16/26* (2019.01)
*G16B 15/00* (2019.01)
*G16B 45/00* (2019.01)

(58) Field of Classification Search
CPC ........ G16B 45/00; G16B 50/00; G16B 50/10; G16B 20/00; G16B 20/20; G16B 20/50
See application file for complete search history.

(56) References Cited

U.S. PATENT DOCUMENTS

2008/0194415 A1* 8/2008 Szabadka ............... G16C 20/80 506/2
2013/0304432 A1* 11/2013 Sander ................... G16B 30/10 703/2
2020/0387550 A1* 12/2020 Cappetta ............. G06F 16/9538
2022/0348903 A1 11/2022 Ranganathan et al.
2022/0391667 A1* 12/2022 Law ........................ G06V 10/76
2025/0378914 A1* 12/2025 Candido ................ G16B 40/20

OTHER PUBLICATIONS

Huysmans et al., "SESAM: A Relational Database for Structure and Sequence of Macromolecules," Proteins: Structure, Function, and Bioinformatics, Sep. 1991, 11(1):59-76.

Kuang et al., "DOMMINO 2.0: integrating structurally resolved protein-, RNA-, and DNA-mediated macromolecular interactions," Database, Jan. 2016, 2016:bav114, 12 pages.

Martinez, "Exploiting Protein Fragments in Protein Modelling and Function Prediction," Doctoral Thesis UPF, 2014, 161 pages.

Mylvaganam et al., "Structural Proteomics: Methods in Deriving Protein Structural Information and Issues in Data Management," BioTechniques, Mar. 2002, 32(sup3):42-46.

* cited by examiner

400

425

450

500

MAINTAINING HIERARCHICAL REPRESENTATION OF A PROTEIN COMPLEX

BACKGROUND

Protein complexes are one or more protein molecules that interact to perform specific biological functions. Each protein molecule within a complex is composed of amino acid sequences, which define its structure and function. These amino acid sequences are derived from DNA sequences through the biological processes of transcription and translation. As such, protein complexes represent a link between genetic information and functional molecular machinery in living organisms.

The study and engineering of protein complexes are central to biotechnology. Applications include the development of therapeutic antibodies, enzyme systems for industrial processes, and molecular tools for diagnostics. Designing protein complexes with particular properties requires precise control over their structural components, which in turn depends on accurate modeling of their DNA and amino acid sequences.

To support these efforts, protein complexes are increasingly represented and stored in computer systems. These representations allow researchers to design, analyze, and simulate protein structures at scale. However, the complexity and diversity of protein designs present challenges for consistent and biologically valid modeling. As a result, there is a growing need for techniques that can efficiently and accurately represent protein complexes in structured, reusable formats.

SUMMARY

This specification describes a system implemented as computer programs on one or more computers in one or more locations that maintains data for a hierarchical representation of a protein complex that includes components and automatically generates missing component data of the hierarchical representation of the protein complex.

Particular embodiments of the subject matter described in this specification can be implemented so as to realize one or more of the following advantages.

Protein design is a foundational task in biotechnology. The ability to engineer proteins with specific structural and functional properties enables the development of novel therapeutics, and industrial enzymes. However, the space of potential protein designs is exponentially large due to the combinatorial explosion of possible DNA, or amino acid sequences. This vast design space presents a significant challenge for the exploration and identification of biologically useful and relevant protein complexes.

One challenge arises from the computational processing and storage burden associated with modeling and managing large numbers of protein complex variants. For example, storing millions of candidate protein complexes on a computer system can result in redundant copies of similar or identical components across different protein complexes, leading to unnecessary duplication in both storage and computational workflows.

Moreover, existing methods for storing and representing protein complex data are often free-form and lack standardized structure. So, the representation of the protein complex could include inherent errors that are not readily apparent. Additionally, the protein complex can be represented differently by different users or systems, introducing inconsistencies and errors that are difficult to detect or reconcile. These errors and inconsistencies can propagate through downstream workflows, leading to incorrect modeling assumptions, failed experiments, or misinterpretation of results.

The described techniques address these challenges by providing a structured, constraint-driven representation of protein complexes using format templates and hierarchical component relationships. The described techniques enable efficient storage, automatic inference of missing data through biological transformations, and consistent modeling across users and applications. As a result, the described techniques facilitate scalable protein design through the improved computational efficiency of processing data representing protein complexes. The described techniques also reduce error rates of stored data representing protein complexes. As a consequence, the described techniques can be applied to improve high-throughput screening and production workflows involving protein complexes.

By maintaining, in a relational database, a plurality of format templates, where each format template defines a hierarchical representation of a protein complex and defines one or more structure constraints between components of the protein complex, the described techniques provide a standardized and reusable framework for modeling protein structures. The format template addresses the challenge of inconsistent and error-prone representations by enforcing structural constraints and enabling uniformity across users and applications.

Because each hierarchical representation of a protein complex has a plurality of component slots representing respective portions of the protein complex, the described techniques enable modular design that is constrained to always be valid because only appropriate slots can be filled based on predefined structural and functional compatibility rules. These constraints ensure that only biologically plausible configurations are permitted, reducing the likelihood of invalid or nonfunctional protein designs.

Additionally, because a database stores records for a plurality of components, where each component includes data representing a respective molecular entity that can serve as one or more portions of the protein complex, the described techniques support efficient data reuse and minimizes duplication. That is, a single component can be associated with one or more component slots and can be associated with one or more hierarchical representations. Thus, only a single copy of the component can be used (e.g., referenced) many times, which reduces memory requirements and improves processing efficiency, while also ensuring consistency and traceability across protein designs.

By storing links representing parent and child relationships between components of the protein complex in the database, the described techniques support error detection, facilitates data propagation, and ensures biological coherence across all levels of the protein complex, addressing the challenge of maintaining accurate and complete representations.

Using the above described features of the database, the described techniques can receive user input specifying a component of a protein complex and a component slot of a format template and populate the relational database with a record representing the component while enforcing the one or more structural constraints of the format template. User provided component data can therefore be validated and integrated correctly, reducing the risk of modeling errors and improving the reliability of downstream workflows.

Also, in response to determining that one or more components in the hierarchical representation has incomplete data (e.g., a parent or child component in the hierarchical representation has incomplete data), the described techniques can automatically generate component data for the one or more components in the hierarchical representation (e.g., for the parent or child component) according to one or more biological transformations. These biological transformations, such as concatenation, decomposition, translation, and back translation, allow the described techniques to infer incomplete data and maintain a complete and biologically valid representation. The described techniques therefore improve data integrity by eliminating manual copying and manual inference, which are prone to human error, inconsistency, and omission. Also, automated data generation ensures that inferred component data are biologically coherent and structurally valid, thereby maintaining the fidelity of the overall protein complex representation. These capabilities therefore support scalable protein design and production.

The details of one or more embodiments of the subject matter of this specification are set forth in the accompanying drawings and the description below.

Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1A:
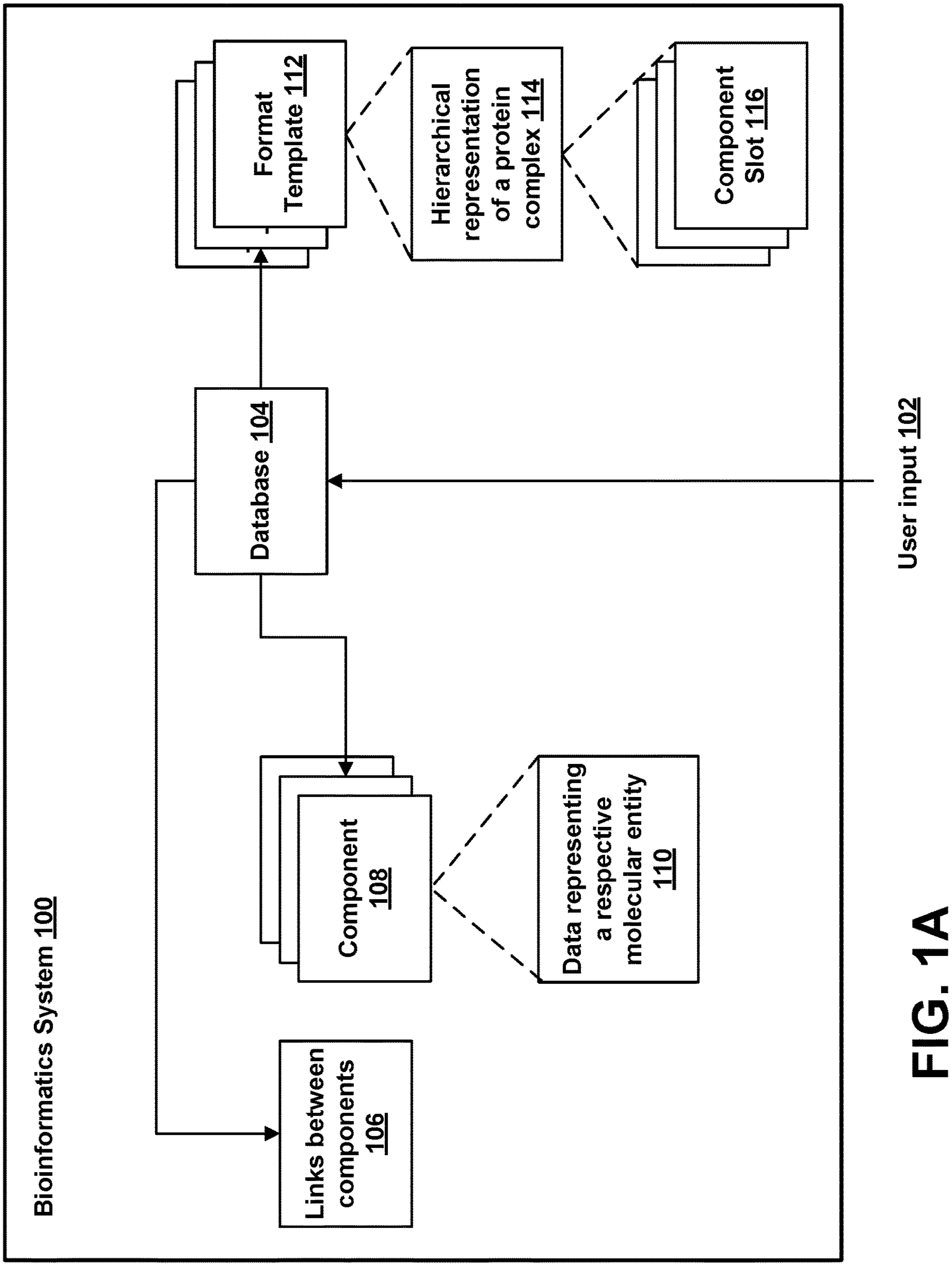
FIG. 1A shows an example bioinformatics system.

FIG. 1A shows an example bioinformatics system 100. The bioinformatics system 100 is an example of a system implemented as computer programs on one or more computers in one or more locations, in which the systems, components, and techniques described below can be implemented.

The bioinformatics system 100 maintains a relational database 104 that in turn maintains data of a hierarchical representation of a protein complex.

The protein complex can be any of a variety of types of protein complexes with any structure, function, and biological role. For example, the protein complex can be an antibody (immunoglobulin), enzyme complex (e.g., DNA polymerase complex), signal transduction complex (e.g., G-protein Coupled receptor complex), membrane protein complex (e.g., ATP Synthase), and so on.

The hierarchical representation of a protein complex can refer to any organization of the structural and functional components of the protein complex.

As an example, for an antibody protein complex, the hierarchical representation can include components for light chains, heavy chains, variable domains of the chains, constant domains of the chains, hinge regions, and so on.

As another example, for an enzyme complex, the hierarchical representation can include components for catalytic subunits, regulatory subunits, cofactor-binding domains, and active sites.

As another example, for a signal transduction complex, the hierarchical representation can include components for membrane-bound receptors, adaptor proteins, kinases, and scaffold proteins.

Generally, a protein complex is defined in terms of amino acid sequences, where amino acid chains and amino acid domains serve as the structural foundation of the protein complex, with amino acid chains representing parent components and amino acid domains representing child components.

More specifically, the system 100 maintains a plurality of format templates 112.

Each format template 112 defines a hierarchical representation of a protein complex 114, where each hierarchical representation of a protein complex 114 has a plurality of component slots 116 representing respective portions of the protein complex. Additionally, each format template 112 defines one or more structure constraints between components of the protein complex.

A component slot 116 serves as a placeholder within a format template 112. It represents a specific portion of a protein complex. For example, it can represent a polypeptide chain (e.g., heavy or light chain), a domain within a chain (e.g., variable or constant domain), a region (e.g., hinge region or antigen-binding site), a functional subunit (e.g., catalytic subunit or receptor domain) and so on. These component slots 116 enable the system 100 to flexibly model diverse protein complexes by defining expected components and their structural relationships.

Figure 1B:
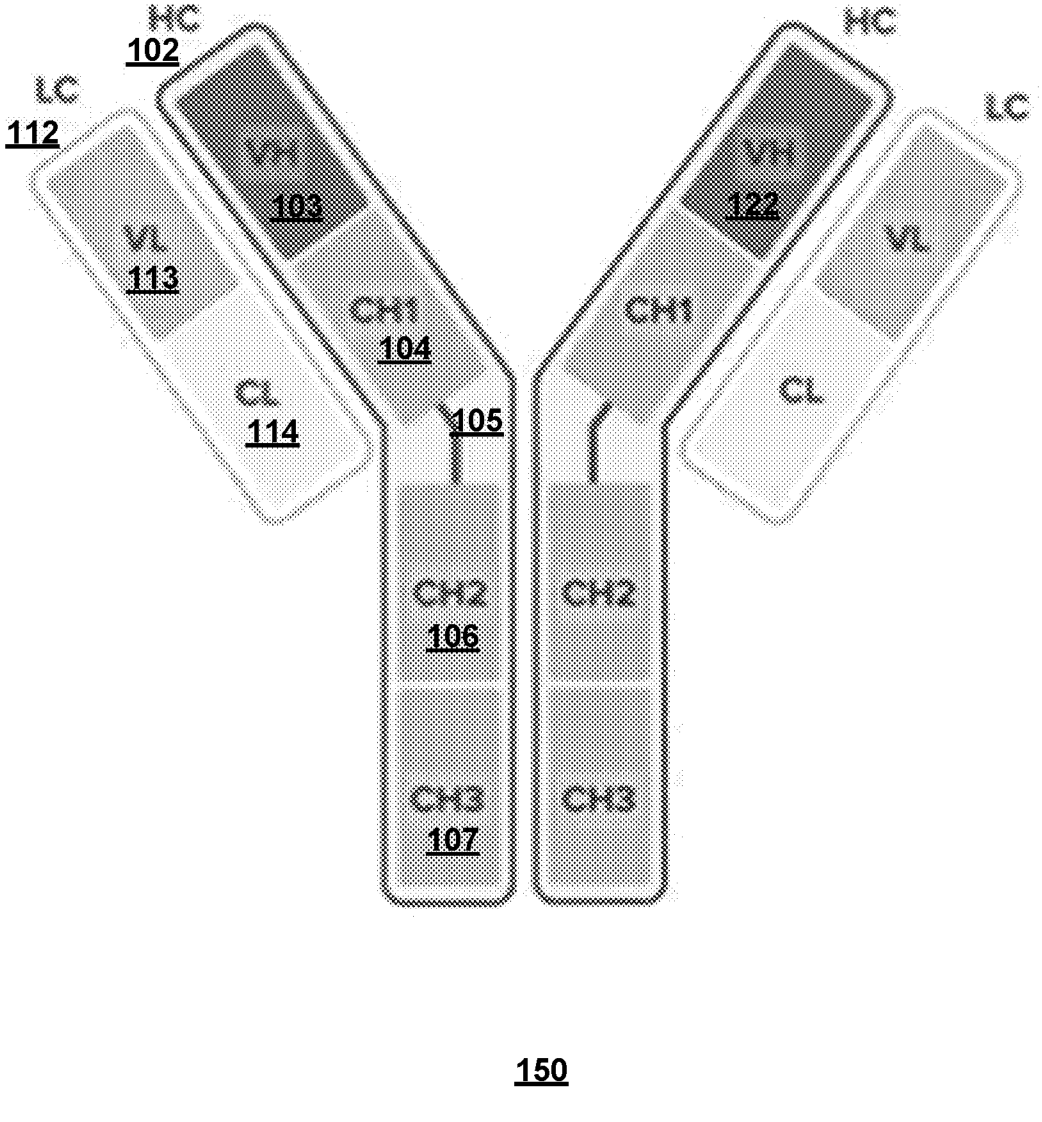
FIG. 1B shows an example illustration of a protein complex.

FIG. 1B is an example 150 visualization of a protein complex with the components belonging to a format template labeled on the visualization. In particular, example 150 is a visualization of an antibody protein complex. For example, the heavy chain (HC) component slot, with subcomponent slots for domains such as VH 102, CH1 104, hinge 106, CH2 106, and CH3 107 are indicated in the visualization. Similarly, the light chain (LC) 112 with subslots for VL 113 and CL 114 are indicated. Additional component slots may represent the hinge region in isolation, a Fab region (composed of VH 103, VL 113, CH1 104, and CL 114), and an Fc region (composed of CH2 106 and CH3 107). In this example, the protein complex has a symmetrical structure, and thus in some implementations the system may only require the user to input or specify half of the component slots. Alternatively or in addition, the system can receiver user input to specify the other depicted component slots, e.g., VH 122.

Thus, component slots correspond to structurally and functionally distinct portions of the protein complex and allow the system 100 to represent the protein complex in a modular and hierarchical manner.

The structure constraints of the format templates 112 are rules that define how components within a protein complex are defined and how they relate to one another. These constraints ensure that the hierarchical representation 114 reflects biologically valid configurations. Examples of structure constraints include naming constraints (e.g., a component slot must include name for the component slot, e.g., a heavy chain component slot must include a name, such as "HC" or "Heavy Chain"), connectivity constraints (e.g., VH must be adjacent to CH1 in FIG. 1B or the hinge region must separate the Fab and Fc regions in FIG. 1B), multiplicity constraints (e.g., exactly two light chains per antibody in FIG. 1B), and composition constraints (e.g., the Fab region must include both VH, VL, CH1, and CL in FIG. 1B).

The database 104 stores records for a plurality of components 108. Each component 108 includes data representing a respective molecular entity 110 that can serve as one or more portions of the protein complex. Through the database 104 records for a plurality of components 108, the system 100 can maintain a hierarchical representation of a protein complex.

A molecular entity 110 broadly refers to any biological molecule or molecular structure that contributes to the makeup or function of a protein complex. Examples of molecular entities include amino acid sequences, which define the primary structure of protein domains and chains; and DNA sequences, which serve as the genetic blueprint for the transcription and translation of the protein components.

While the system supports DNA sequences as molecular entities, their use is optional. DNA sequences can be used to generate amino acid sequences via translation or inferred from amino acid sequences via back translation, but the general representation of protein complexes are amino acid sequences.

The system 100 can enforce constraints (e.g., those described above) because it maintains type information for each named entity. Type can refer to a classification or label that defines the biological role, structural category, or molecular nature of a component. For example, a component may be typed as a "domain," "chain," "region," or "subunit," and may further be typed by its molecular entity, such as "amino acid sequence" or "DNA sequence." The type information allows the system 100 to validate compatibility between components, enforce structural rules (e.g., only domains can be nested within chains), and ensure that the hierarchical relationships conform to biologically plausible configurations.

In some cases, the system 100 can further support subtype labeling for specific instances of chains and domains. For example, a domain used in a variable heavy (VH) slot can be labeled with a type field having a value "VH," and a chain used in a heavy chain slot can be labeled with a type field having a value "heavy." This additional layer of typing enables more granular validation and facilitates accurate modeling of component roles within complex protein architectures.

Additionally, some structural constraints specify connection types between components. A connection type refers to the nature of the biological or chemical linkage between components, such as peptide bonds between amino acid sequences, disulfide bridges between cysteine residues, or linker sequences between domains. These connection types help define how components are physically or functionally joined within the protein complex. For example, a format template may require that the VH domain be connected to the CH1 domain via a peptide bond, or that a hinge region connects the CH1 and CH2 domains through a flexible linker. By maintaining type and connection type information, the system 100 ensures that only biologically plausible and structurally valid configurations are modeled and stored.

In some cases, each component includes data representing a plurality of respective molecular entities that can serve as one or more portions of the protein complex. For example, a component may include data representing a DNA sequence and the corresponding amino acid sequence corresponding to a biological translation of the DNA sequence.

In some implementations, the system 100 can validate that the molecular entities associated with components. For example, the system 100 can validate that the amino acid sequence associated with a component contain the required residues at appropriate positions to support the specified connection types. For example, in the case of a disulfide bridge, the system 100 can confirm the presence and location of cysteine residues in the relevant sequences to ensure that such a bond is present.

In some implementations, the system 100 maintains translation links between DNA and amino acid sequences. These links validate that the DNA sequence encodes the exact amino acid sequence through biologically accurate codon mappings. Translation links also provide traceability between molecular entities and ensure biological fidelity across sequence types.

In some implementations, the system 100 supports many-to-one relationships between DNA and amino acid sequences. That is, multiple distinct DNA sequences can be linked to a single amino acid sequence, reflecting codon redundancy in biological encoding. This capability allows the system 100 to track all DNA variants that encode a given protein complex, supporting design flexibility and experimental reproducibility.

In addition to storing records for a plurality of components 108, the database 104 stores links 106 representing parent and child relationships between components of the protein complex, enabling the system 100 to model, store, and maintain the hierarchical representation and structure of a protein complex. For example, these links define how components 108 are nested within larger ones, e.g., a heavy chain component having domains components such as VH, CH1, CH2, and CH3 as indicated in the visualization of FIG. 1B.

As a particular example, in the case of an antibody protein complex, the system 100 can store records for the entire antibody (i.e., store and maintain a hierarchical representation of a protein complex). This antibody would have child links to other components 108, such as heavy chains and light chains, which in turn have child links to other components 108, e.g., to their respective domains, such as VH, CH1, CH2, and CH3 for the heavy chain, and VL and CL for the light chain. These parent/child relationships can be stored as links 106. Each component 108 can include its amino acid sequence (i.e., data representing the respective molecular entity 110), which defines its structure, and optionally further include to the DNA sequence that encodes it (i.e., data representing the respective molecular entity 110). This hierarchical linking allows the system 100 to trace the structural lineage of each portion of the protein complex.

In some cases, the links 106 include "part links." That is, in addition to parent-child links, the system 100 maintains "part links" that govern the relationships between chains and their constituent domains. These links validate that the domain sequences are fully contained within the corresponding chain sequences, down to the exact nucleotide (for DNA sequences) or amino acid (for amino acid sequences) level. This containment validation ensures structural integrity and supports automated verification of component inclusion.

To populate the relational database 104 with a record representing a component 108, the system 100 receives user input 102 specifying a component of a protein complex and a component slot 116 of a format template 112.

The system 100 can receive this user input 102 using any of a variety of methods. For example, the system 100 can receive the user input 102 from a user interaction through a user device (e.g., a laptop computer, a smart phone, a tablet computer, and so on). For example, the interactions can include keyboard and mouse inputs, touchscreen inputs, or voice commands.

As an example, for the case of an antibody protein complex, the system 100 can receive user input 102 through a web-based interface on a laptop computer. The user can interact with the interface to select a format template 112 for an IgG antibody. In response, the system 100 can present a dropdown menu allowing the user to specify a domain (e.g., VH, i.e., a component slot 116). Upon the user's selection, the system 100 enables the user to upload a corresponding amino acid sequence file (i.e., specified component of the protein complex), which the system 100 receives and interprets as data representing a molecular entity 110.

As another example for the system 100 to receive user input 102, the system 100 can allow the user to click a link to associate a stored DNA sequence (i.e., a specified component of the protein complex) with the VH domain slot (i.e., a component slot 116 of a selected format template 112), or drag and drop a molecular entity from a list of available entities into the appropriate slot 116 in the format template 112.

Through these user inputs, the system 100 maps the specified molecular entity (i.e., component of the protein complex) to the corresponding structural component slot 116 of the protein complex.

In some cases, the system 100 further supports custom molecular entities. For example, the system 100 can map a custom specified molecular entity to the corresponding structural components slot(s) 116 of the protein complex.

As an example custom entity, a custom entity can be a "pair," which refers to two protein domains that together form the antigen-binding site of an antibody, such as the variable heavy (VH) and variable light (VL) domains. So, a custom entity can model a pair that includes fields referencing the individual VH and VL domains, and a user can select such a custom entity for the system 100 to simultaneously map the corresponding molecular entities to two component slots of a format template, thereby streamlining the input process and preserving the biological relationship between the paired domains.

Once the system 100 receives the user input, the system 100 populates the relational database 104 with a record representing the component 108 while enforcing the one or more structural constraints of the format template 112.

The system 100 enforces the structural constraints defined in the format template 112 to ensure that the resulting representation is biologically valid. For example, the system 100 can verify that required components 108 are present, that their relationships conform to expected connectivity and orientation rules, and that multiplicity constraints (e.g., number of chains or domains) are satisfied. The system 100 can also validate the molecular entity data (e.g., sequence format, length, compatibility, or content) before finalizing the record. Enforcing the structural constraints of the format template 112 ensures that the hierarchical model of the protein complex remains consistent, accurate, and usable for downstream tasks.

In addition to maintaining data of a hierarchical representation of a protein complex, the system 100 can automatically generate component data for the hierarchical representation of the protein complex. That is, when the system 100 receives component data (e.g., a specified component) for a particular component slot of the protein complex, it can determine, e.g., through the stored links between components 106, that one or more components in the hierarchical representation has incomplete data (e.g., a parent or child component) in the hierarchical representation has incomplete data. Then, in response, the system 100 can automatically generate component data for the one or more components in the hierarchical representation that has incomplete data (e.g., the parent or child component) according to one or more biological transformations.

For example, consider an antibody protein complex and a format template 112 that specifies that a light chain must include two domain components, e.g., a variable domain (VL) and a constant domain (CL). The system 100 can receive component data for the antibody light chain that includes its full amino acid sequence, and because the light chain component has child links to these domain components, and the provided amino acid sequence contains all the sequence information necessary to define both domains, the system 100 can automatically generate component data for the VL and CL domain components. This generation may include the system 100 extracting the relevant subsequences from the full chain sequence, assigning them to the appropriate domain component slots, and linking them to the corresponding molecular entities (e.g., amino acid and/or DNA sequences). In doing so, the system 100 ensures that the hierarchical representation remains complete and consistent, even when only partial input is initially provided.

Conversely, for the case of the previous example, if the system 100 received component data for the VL domain instead of the component data for the light chain, the system 100 can partially populate the component data of the light chain using the component data of the VL domain. That is, because the VL domain is linked as a child of the light chain component, and the format template 112 defines the light chain as composed of both VL and CL, the system 100 can automatically generate partial component data for the light chain. This generation may include the system 100 creating a light chain component record, associating the VL domain as a child, and marking the CL domain as missing or pending. The system 100 may also infer the partial amino acid sequence of the light chain based on the VL domain and link it to the corresponding molecular entities. In doing so, the system 100 begins constructing the parent component and maintains consistency in the hierarchical representation, even when only a subcomponent is initially provided.

More specifically, while the system 100 maintains a hierarchical representation of a protein complex, the system 100 receives user input 102 that includes component data defining a particular molecular entity for a particular component slot of the protein complex.

The system can receive this user input from any of variety of sources, such as file uploads, API calls, or selections made through a user interface (e.g., a graphical user interface). The component data, as described above, includes data representing a respective molecular entity. Examples of molecular data, as described above, includes biological sequence information, such as amino acid or DNA sequences and is associated with a specific structural or functional portion of the protein complex as defined by the format template 112.

As an example, a user can upload an amino acid sequence file for an antibody light chain through a web interface. The system 100 receives this input and associates the sequence with the light chain component slot 116 of the selected format template 112.

The system 100 determines that one or more components in the hierarchical representation has incomplete data (e.g., a parent or child component in the hierarchical representation has incomplete data). That is, the system 100, based on evaluating the format template 112 that the hierarchical representation is derived from and the stored links 106 between components 108, determines that the one or more components in relation to the received component has incomplete data (e.g., a parent or child component to the received component has incomplete data).

For example, if the system 100 receives component data for the VL domain of an antibody light chain that requires two domains, it checks the format template and determines that the light chain is the parent component to the provided VL domain. Since no data has been provided for the parent component, the system 100 identifies the VL domain as a partial component for the light chain component.

The system 100, in response, automatically generates component data for the one or more components with incomplete data (e.g., for the parent or child component) according to one or more biological transformations (e.g., as described above).

Examples of biological transformation include concatenation, decomposition, translation, and back translation.

Concatenation can refer to combining molecular data from child components to infer the parent component. As one example, DNA sequences of VL and CL can be combined to infer the DNA of the light chain. As another example, DNA chains can be assembled into plasmids.

Decomposition can refer to splitting molecular data from a parent component to infer child components. As one example, domain sequences can be extracted from a full chain sequence. As another example, plasmids can be scanned for DNA chains.

Translation can refer to converting DNA to amino acid sequences.

Back translation can refer to inferring DNA sequences from amino acid sequences using codon tables or heuristics.

These biological transformations allow the system 100 to infer and populate missing component records using available molecular entity data, ensuring biological validity and completeness.

In some implementations, the system 100 further preserves metadata (e.g., sequence characterization features, such as annotations indicating design intent, molecular function, or biological meaning) across biological transformations. For example, when sequences are concatenated, translated, or decomposed, associated annotations can be retained and appropriately mapped to the resulting sequences. The system 100 can therefore ensure that the functional and contextual metadata of the original molecular entities is not lost during transformation, thereby maintaining the integrity and interpretability of the data.

As an example, if the system 100 receives a DNA sequence for the VL domain, it can perform translation to generate the corresponding amino acid sequence. Then, using the format template 112, the system 100 can infer the partial amino acid sequence of the parent light chain, create a light chain component record, associate the VL domain as a child, and prompt a user for the CL domain. This automated generation helps maintain a consistent and complete hierarchical representation, even when only partial data is initially provided by the user.

In some implementations, the system 100 includes a format template creation tool that enables users to define new format templates. For example, the system can use the tool to allow users to (a) define chains by ordering domains and assigning a multiplicity to each domain, and (b) assemble chains in physical space using a drag-and-drop interface.

Figure 2:
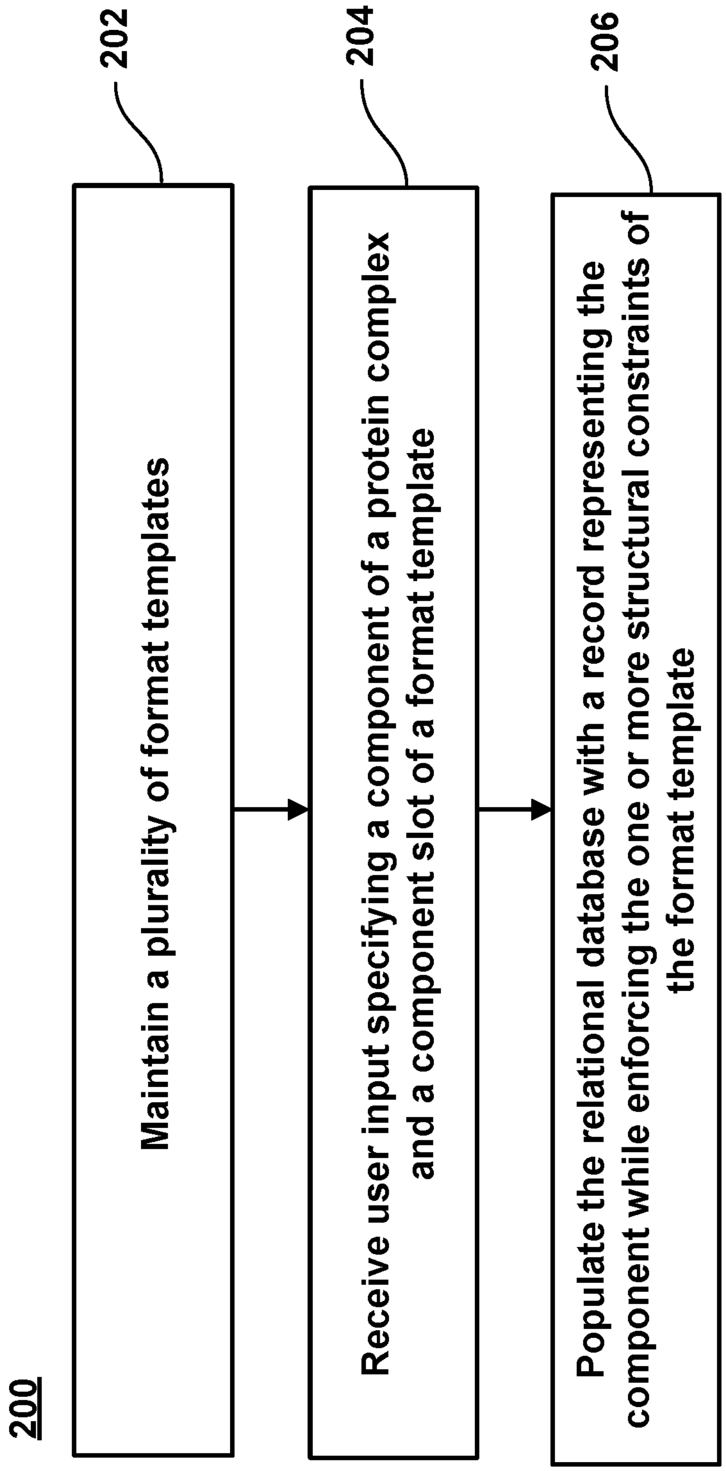
FIG. 2 is a flow diagram of an example process for maintaining data of a hierarchical representation of a protein complex.

FIG. 2 is a flow diagram of an example process 200 for maintaining data of a hierarchical representation of a protein complex. For convenience, the process 200 will be described as being performed by a system of one or more computers located in one or more locations. For example, a bioinformatics system, e.g., the bioinformatics system 100 of FIG. 1A, appropriately programmed in accordance with this specification, can perform the process 200.

The system maintains, in a relational database, a plurality of format templates (step 202). The database additionally stores records of components and links representing parent and child relationships between components of the protein complex.

As described above, each component includes data representing a respective molecular entity that can serve as one or more portions of the protein complex. For example, a component can include data representing an amino acid sequence that can serve as one or more portions of the protein complex.

In some cases, each component includes data representing a plurality of respective molecular entities that can serve as one or more portions of the protein complex. For example, a component can include data representing an amino acid sequence and the amino acid sequence's corresponding DNA sequence.

As described above, these format templates define hierarchical representations of protein complexes, where each hierarchical representation of a protein complex has a plurality of component slots representing respective portions of the protein complex. Additionally, each format template defines one or more structure constraints between components of the protein complex.

A single type of protein complex can be represented by multiple format templates, each capturing a distinct structural or functional variant.

For example, an antibody protein complex can include multiple format templates that represent different classes, subclass, and engineered configurations of an antibody, e.g., IgG, IgA, scFv, Fab, or bispecific formats.

In some cases, the one or more structural constraints of the format template specify connection types that must be present or absent between components of the format template. As described above, connection types refer to the specific biological linkage, chemical linkages, or structural linkage that define how components are joined within the protein complex.

For example, for an antibody protein complex, a format template may specify that the VH domain must be directly connected to the CH1 domain (an example of a structural linkage and a connectivity constraint), enforcing a biologically valid domain arrangement in the heavy chain, as illustrated in FIG. 1B.

As another example, a format template may specify that the hinge region must connect the CH1 domain to the CH2 domain (an example of a structural linkage and a connectivity constraint), ensuring that the flexible linker between the Fab and Fc regions is properly represented, as illustrated in FIG. 1B.

As another example, a template can specify that two heavy chains are connected via disulfide bonds, enforcing inter-chain connectivity constraints (a type of connectivity constraint that reflects the quaternary structure of the antibody).

The system can enforce these constraints by evaluating the type and molecular entity data of each component and validate that the specified connection types are compatible with the biological roles and structural relationships defined in the format template.

In some cases, the connection types of the format template are based on molecular entity types of connected components of the protein complex.

For example, a format template may specify that a connection between two components is only valid if both components are represented by amino acid sequences, thereby enforcing a peptide bond constraint (an example of a biological or chemical linkage).

In some cases, the one or more structural constraints of the format template specify which component types can or must not appear in component slots of the format template. These constraints define the allowable structural composition of the protein complex and prevent biologically invalid configurations.

For example, a format template for a scFv antibody can specify that Fc region components must not be present, since scFv formats lack the Fc domain and consist only of linked variable domains.

As another example, a format template for an IgG antibody can include a structural constraint that allows the user to specify only one half of the antibody protein complex, such as one heavy chain and one light chain, because the IgG molecule is symmetrical. The system can then automatically mirror the specified half to complete the full antibody structure. This structural constraint reduces user burden and helps prevent modeling errors by ensuring that the resulting protein complex aligns with the expected symmetrical structure of the IgG format.

The system receives user input specifying a component of a protein complex and a component slot of a format template (step 204).

Specifying a component of a protein complex includes providing data representing a respective molecular entity that can serve as one or more portions of the protein complex. This molecular entity may be an amino acid sequence, DNA sequence, or other biological data that defines the structure or function of a component, as described above.

Specifying a component slot of a format template refers to identifying the structural or functional position within the format template where the molecular entity should be placed. Each component slot corresponds to a defined portion of the protein complex, such as a domain, chain, region, or subunit, and is governed by the structural constraints of the format template.

In some implementations, the system can generate a user interface that presents the hierarchical representation of a protein complex to a user through a user device, such as a desktop computer, laptop, tablet, or smartphone. The system can allow the user to select a format template through the user interface, view the protein complex structure the selected template corresponds to, and populate the component slots of the format template with molecular entity data.

For example, the system can present a visual interface on a desktop computer where the user selects a format template for an IgG antibody. The system displays, through the interface, a schematic of the antibody structure, including labeled component slots for heavy chains, light chains, variable domains, constant domains, hinge region, Fab region, and Fc region. The user can click on a slot (e.g., the VH domain) to upload an amino acid sequence file or select a stored DNA sequence from a dropdown list. The system then maps the uploaded or selected molecular entity to the corresponding component slot in the format template.

In some implementations, the user interface visually illustrates the component slots of the format template and identifies corresponding components stored in the database. For example, the user can interact with the interface (e.g, by clicking on a component slot) to view or edit the underlying data, such as amino acid sequences, domain annotations, or linked components. This interactive visualization helps users understand the structure of the protein complex and manage its components efficiently.

The system populates the relational database with a record representing the component while enforcing the one or more structural constraints of the format template (step 206).

For example, upon receiving user input that specifies a molecular entity and a corresponding component slot, the system creates a new database record for the component and associates it with the designated slot in the selected format template. The system then evaluates the structural constraints defined in the format template to ensure that the new component is valid within the context of the hierarchical representation.

The enforcement can include verifying that the component is compatible with its neighboring components (e.g., child/parent components) based on defined connection types, ensuring that required components are present, and confirming that disallowed components are absent. The system can also check multiplicity constraints (e.g., the number of chains or domains allowed), orientation constraints (e.g., ordering of domains), and composition constraints (e.g., required subcomponents).

In some cases, if the component includes molecular entity data, such as sequence data, the system can validate the format, length, and biological plausibility of the sequence before finalizing the record. As a specific example of validating the biological plausibility of the sequence the system can check for the presence of premature stop codons in an amino acid sequence, which indicates that the sequence is unlikely to produce a functional protein and therefore may be biologically invalid in the context of the intended component slot.

In some cases, the record representing the component includes metadata of the component. Some examples calculated molecular weight, extinction coefficient, predicted solubility, isoelectric point, and other physicochemical properties that help characterize the behavior and suitability of the component within the protein complex. This metadata can be used for downstream analysis, such as assessing expression feasibility, purification strategies, or functional performance.

In some cases, the system can apply format-specific logic to calculate molecular entity data (e.g., biochemical properties of the entire protein complex and/or its components). For example, by aggregating the amino acid sequences of all components, accounting for their assigned multiplicities, and modeling how chains are physically assembled, the system can compute properties such as total molecular weight, net charge, or expected solubility of the full complex. Because format templates define consistent structural and spatial rules, the system can apply reusable calculations across different formats to support automated, scalable analysis of complex-level properties.

In some cases, the system stores each unique component only once in the database, regardless of how many component slots and protein complex designs reference it. That is, rather than duplicating the component record for each component slot or protein complex design that references it, the system uses a reference pointer to associate the component with multiple component slots across different hierarchical representations. By only storing one copy of unique component, the system reduces memory usage, improves processing efficiency, and ensures consistency and traceability across all protein designs that reuse the same component.

Once the system finishes validating the component, it links the new component to related components in the hierarchy using stored parent-child relationships, and stores the component data, which include metadata and molecular entity references, in the relational database.

Figure 3:
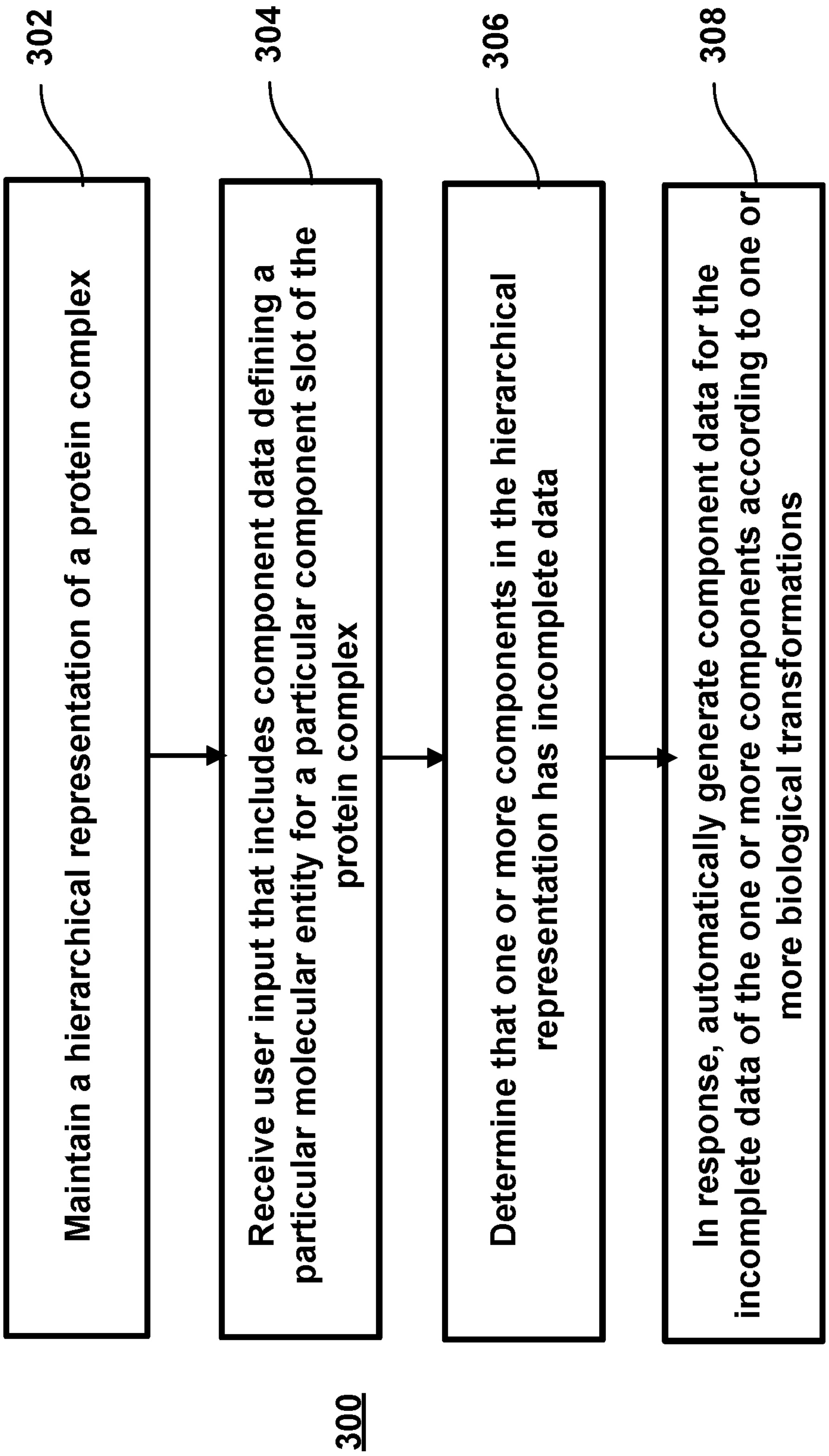
FIG. 3 is a flow diagram of an example process for automatically generating component data of a hierarchical representation of a protein complex.

FIG. 3 is a flow diagram of an example process 300 for automatically generating component data of a hierarchical representation of a protein complex. For convenience, the process 300 will be described as being performed by a system of one or more computers located in one or more locations. For example, a bioinformatics system, e.g., the bioinformatics system 100 of FIG. 1A, appropriately programmed in accordance with this specification, can perform the process 300.

The system maintains, in a relational database, a hierarchical representation of a protein complex (step 302).

The system maintaining the hierarchical representation involves storing components of the protein complex, the relationships or links between those components (such as parent-child associations), and the format template that define structural and functional constraints on how those components can be arranged.

The system receives user input that includes component data defining a particular molecular entity for a particular component slot of the protein complex (step 304). In other words, a user provides data representing a molecular entity(ies) (e.g., a DNA sequence, amino acid sequence, or other biological representation) or custom molecular entity(ies) that corresponds to a specific portion(s) of the protein complex (e.g., a domain, chain, or region), and the user also specifies where in the hierarchical structure this data should be placed, aligning it with a predefined component slot in the format template.

For example, a user may upload an amino acid sequence corresponding to the variable heavy (VH) domain of an antibody and specify that it should be inserted into the VH component slot of an IgG format template. The system then receives this user input and associates the sequence with the designated slot in the hierarchical representation according to the format template.

The system determines that one or more components in the hierarchical representation has incomplete data (step 306). For example, the system determines that a parent or child component in the hierarchical representation has incomplete data.

That is, when the system detects that a related component (e.g., one that contains the specified component (a parent) or one that is derived from it (a child) or the component itself) is missing required molecular entity data, the system determines that the related component in the hierarchical representation has incomplete data. For example, if a user provides a VH domain sequence but the full heavy chain sequence is not yet defined, the system recognizes that the parent component (the heavy chain) is incomplete. Similarly, if a full chain is provided but its constituent domains are not yet defined, the system identifies the child components as incomplete.

This determination is not limited to a single level of the hierarchy but propagates through the entire parent-child graph. For example, if a child component is missing data, its parent may also be considered incomplete because the parent component's molecular entity depends on the child. Likewise, if a parent is missing data, its own parent may be affected, and so on. This recursive evaluation ensures that the system maintains a biologically coherent and complete representation across all levels of the protein complex.

As described above, in some cases, each component includes data representing a plurality of respective molecular entities that can serve as one or more portions of the protein complex. So the system can determine that one or more of the plurality of respective molecular entities is missing. For example, if the system expects a component to include DNA sequence data and amino acid sequence data, when only DNA sequence data is present for the component, the system can determine the component data is incomplete.

The system, in response, automatically generates component data for the incomplete data of the one or more components according to one or more biological transformations (step 308). For example, the system can automatically generate component data for the parent or child component with incomplete data according to one or more biological transformations.

As described above, the biological transformations the system uses include, for example, concatenation, decomposition, translation, and back translation.

Using these biological transformations, the system can automatically infer and generate missing component data. For example, if a user provides a full amino acid sequence for a heavy chain, the system can decompose that sequence to identify and extract the VH, CH1, hinge, CH2, and CH3 domains. Alternatively, if only the VH and CH1 domains are provided, the system can concatenate them to generate a partial heavy chain sequence. If only an amino acid sequence is available for a component, the system can perform back translation to infer a corresponding DNA sequence, selecting codons based on species-specific preferences. These automated inferences ensure that the hierarchical representation remains complete and biologically coherent, even when only partial data is initially provided by the user.

In some cases, the system uses user provided rules to automatically generate component data for the incomplete data of the one or more components according to one or more biological transformations. That is, the user can define transformation preferences, constraints, or biological assumptions that guide how the system performs operations such as translation, back translation, concatenation, or decomposition.

In some cases, in addition to generating component data, the system can also characterize the generated data by assigning metadata attributes. For example, when the system automatically generates a heavy chain sequence, it can set a "type" field of the corresponding entity to "heavy" and can assigns a "species" field based on the species associated with the constituent domains.

By using user provided rules to automatically generate component data for the incomplete data of the one or more components according to one or more biological transformations, the system significantly reduces the need for manual intervention. As a result, users can rapidly construct biologically valid protein complex models with minimal effort, improving both the speed and accuracy of bioinformatics workflows.

For example, a user may specify codon usage tables, or preferred domain boundaries for decomposition. Additionally, a user may define genetic codes for translation processes, or codon usage frequency tables for back translation operations. These rules are applied during the auto-generation process to ensure that the generated component data not only completes the hierarchical representation but also aligns with the user's experimental or design goals. By incorporating user-defined logic into the biological transformations, the system supports flexible and context-aware autocompletion of component data, while maintaining biological plausibility and structural consistency across all levels of the protein complex.

The described techniques can be used to perform a variety of tasks that include maintaining data of a hierarchical representation of a protein complex and automatically generating component data of a hierarchical representation of the protein complex.

For example, the described techniques can be used to enumerate and model a wide range of protein complexes for use in bioinformatics studies, such as high-throughput screening for therapeutic candidates. The system can generate these protein complexes as structured and linked components in the database, each governed by format templates that define their structural constraints. Once stored, the system can perform in silico screening of the complexes to evaluate properties such as binding affinity, solubility, or stability, helping researchers identify promising candidates for further development.

As another example, the system can use the stored hierarchical representation of a protein complex to support the physical generation of the protein complex. For example, if the molecular entity data for each component is stored in the form of DNA sequences in the system database, the system can assemble these sequences into a gene vector suitable for expression in a host organism. Once the vector (or plasmid) is digitally determined in silico by the system, it can be physically generated in vivo (e.g., through DNA synthesis). Then, the physical vector can be introduced into a cell line or other expression system to drive protein production in a laboratory setting. By leveraging the linked, structured component data and the format templates that define valid configurations, the system ensures that the resulting gene construct accurately reflects the intended protein architecture and maintains biological validity.

Enforcing structural constraints through format templates, which prevent invalid configurations from being modeled or stored, and enabling automatic inference of missing component data using biological transformations greatly reduces the potential for errors and reduces the computational overhead of these tasks. Also, because the system can store each unique component only once and reference it across multiple designs, memory usage is minimized, and redundant computations are avoided. Additionally, the hierarchical structure allows for efficient propagation of validated data across related components, eliminating the need for manual repeated entry and reducing the likelihood of inconsistencies. These efficiencies collectively streamline the modeling, analysis, and production of protein complexes, making the system well-suited for high-throughput and scalable bioinformatics workflows.

Additionally, because the system enforces structural constraints and supports automatic data generation, users can rapidly generate diverse variations of protein complexes that have passed all in silico biological checks. The rapid valid and diverse generation of variation of protein complexes enables efficient exploration of design alternatives, accelerates iterative modeling, and ensures that all generated configurations conform to the predefined rules of the format templates. As a result, users can confidently evaluate multiple candidates without the risk of introducing invalid or inconsistent structures.

Figure 4A:
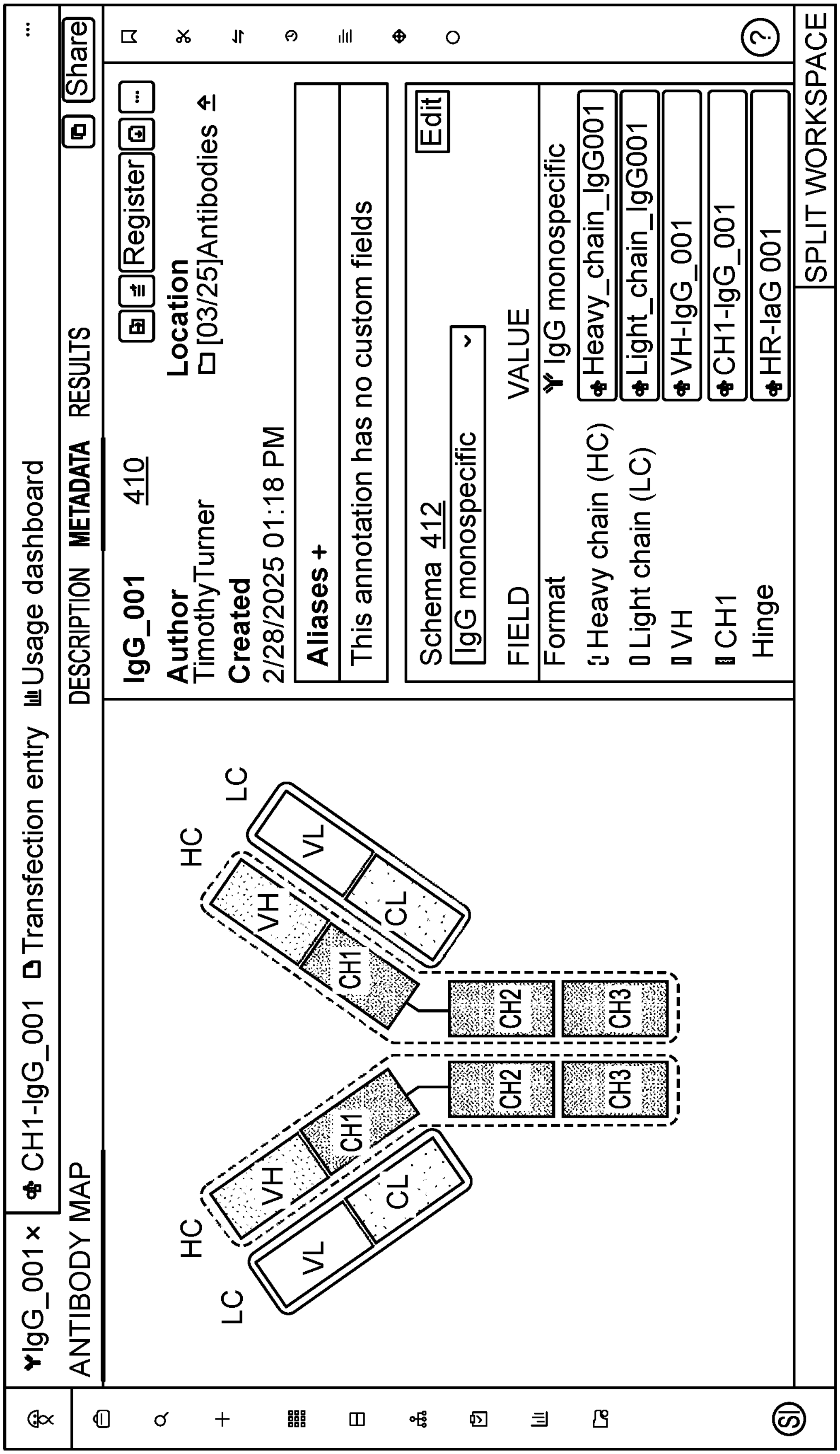
FIG. 4A shows an example user interface presentation.

FIG. 4A shows an example 400 user interface presentation.

In particular, example 400 is an example user interface presented on the display of a user device to a user and can be executed through an electronic lab notebook and biological registry computer program, where a user can provide inputs to the user interface through the use of a mouse and keyboard connected to the computer.

Example 400 displays the hierarchical representation of a protein complex that is an antibody as a 2D map representation. The antibody is visually segmented into its constituent components, such as heavy chains, light chains, variable regions, constant regions, and antigen-binding sites. Each component is rendered as a distinct, selectable graphical element within the interface.

The user interface enables interactive exploration of the antibody structure. In particular, users can select (e.g., click) on any visualized component to access contextual metadata associated with that component. Upon selection, the interface displays a detail panel 410 that can include one or more of the following attributes:

- Author or source of the component data
- Location or origin (e.g., lab, record, or organism)
- DNA or amino acid sequence corresponding to the component data.
- Version history or modification records
- Links to related components or parent/child relationships in a hierarchical model The schema box 412 on the right includes two columns. The first "Field" column includes the components of the protein complex for the selected format template, while the second "Value" column includes references to the components or selected format template. For example, the field titled "format" refers to the format template selection, which in the value column is "IgG monospecific". Other visible field values in the Filed column include the components belonging to the selected format, e.g., Heavy chain (HC), Light Chain (LC), VH, CH1, hinge, and so on. The corresponding entries in the value column are the names of those components.

In some implementations, the user interface further includes a visual coloring scheme that communicates chain identity. For example, in the case of a monospecific antibody, the two heavy chains and two light chains are rendered using the same color to indicate equivalence, with each chain having a multiplicity of two. In contrast, for bispecific antibody formats, the chains on the left and right sides may be rendered using different colors to indicate non-equivalence, with each chain having a multiplicity of one. This visual differentiation facilitates intuitive recognition of structural symmetry or asymmetry within the protein complex.

Figure 4B:
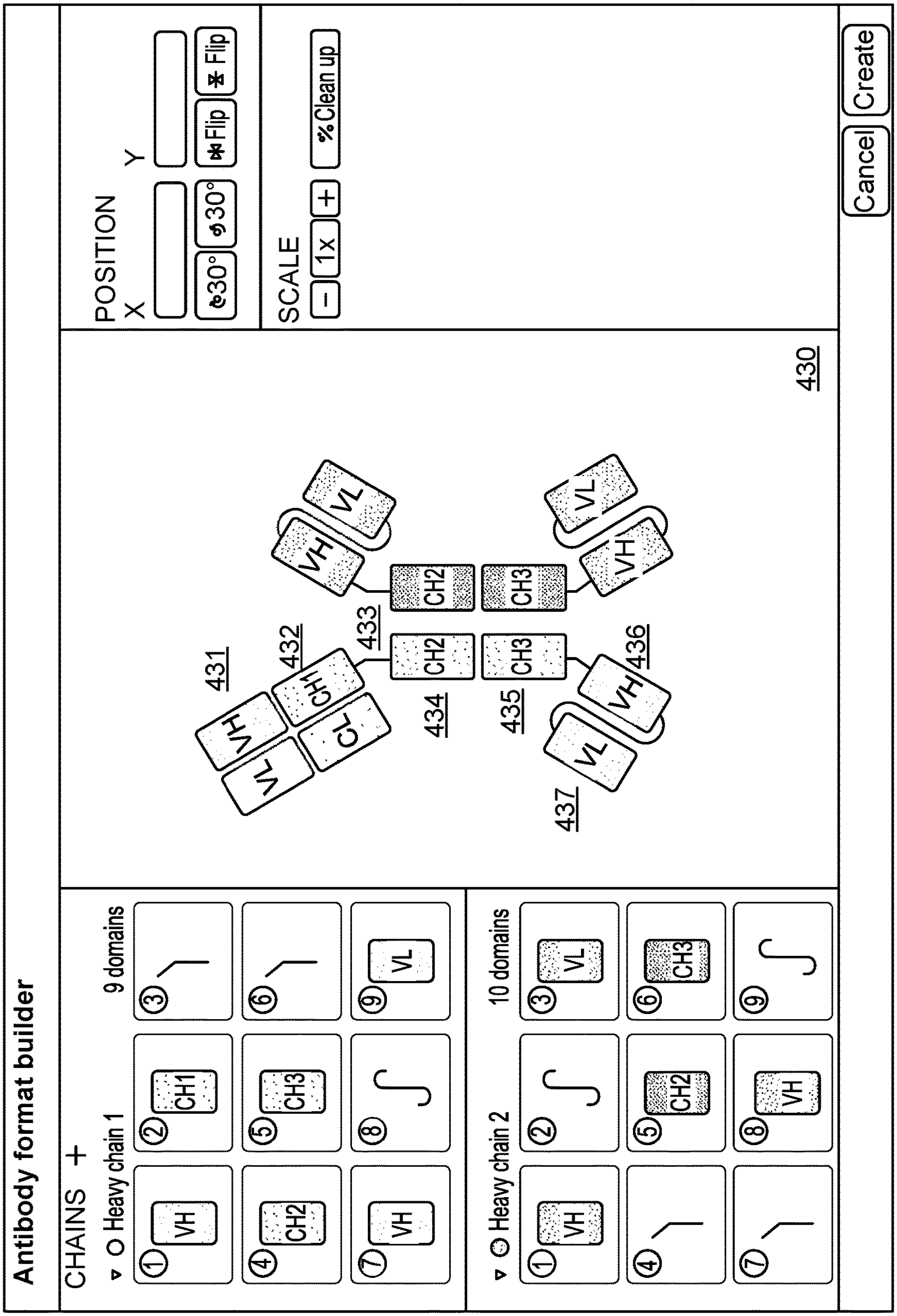
FIG. 4B shows an example user interface presentation.

FIG. 4B shows an example 425 user interface presentation.

In particular, example 425 is an example user interface displayed on a computer monitor to a user and executed through an electronic lab notebook and biological registry computer program, where a user can provide inputs to the user interface through the use of a mouse and keyboard connected to the computer.

Example 425 shows a format configuration tool that enables users to define the structural organization of a protein complex by specifying how individual domains are assembled into chains. The interface includes a drag-and-drop workspace 430 where users can visually construct chains by arranging domain components in a desired order. Each domain is represented as a selectable graphical element, and users can drag these elements into a designated chain assembly area to define the sequence and connectivity of domains within a chain, e.g., by specifying hinge regions. The format configuration tool streamlines the process of designing protein complex templates by providing an intuitive and visual method for specifying domain arrangements and chain compositions, thereby reducing manual errors and improving consistency across designs.

For example, a user can begin with an empty chain scaffold and populate it with domains such as VH 431, CH1 432, hinge 433, CH2 434, and CH3 435 by dragging them into the workspace 430. Additionally, a user can expand the chain by adding VH 436 and VL 437 with one or more additional hinge regions.

Therefore, in some cases, the system's user interface supports interactive customization of format templates. After the user finishes specifying this custom format template, the system can save the custom user format template, which can then be used by the system to model hierarchical representations of protein complexes.

Additionally, the format configuration tool of FIG. 4B, can enforce structural constraints during the design of protein complex templates. When users drag and drop domain components into a chain scaffold, the system can validate the arrangement. For instance, the system can ensure that VH precedes CH1 and that hinge regions are correctly positioned between domains. This enforcement prevents users from creating structurally invalid configurations and ensures that the resulting chain design adheres to biologically accurate models.

Figure 4C:
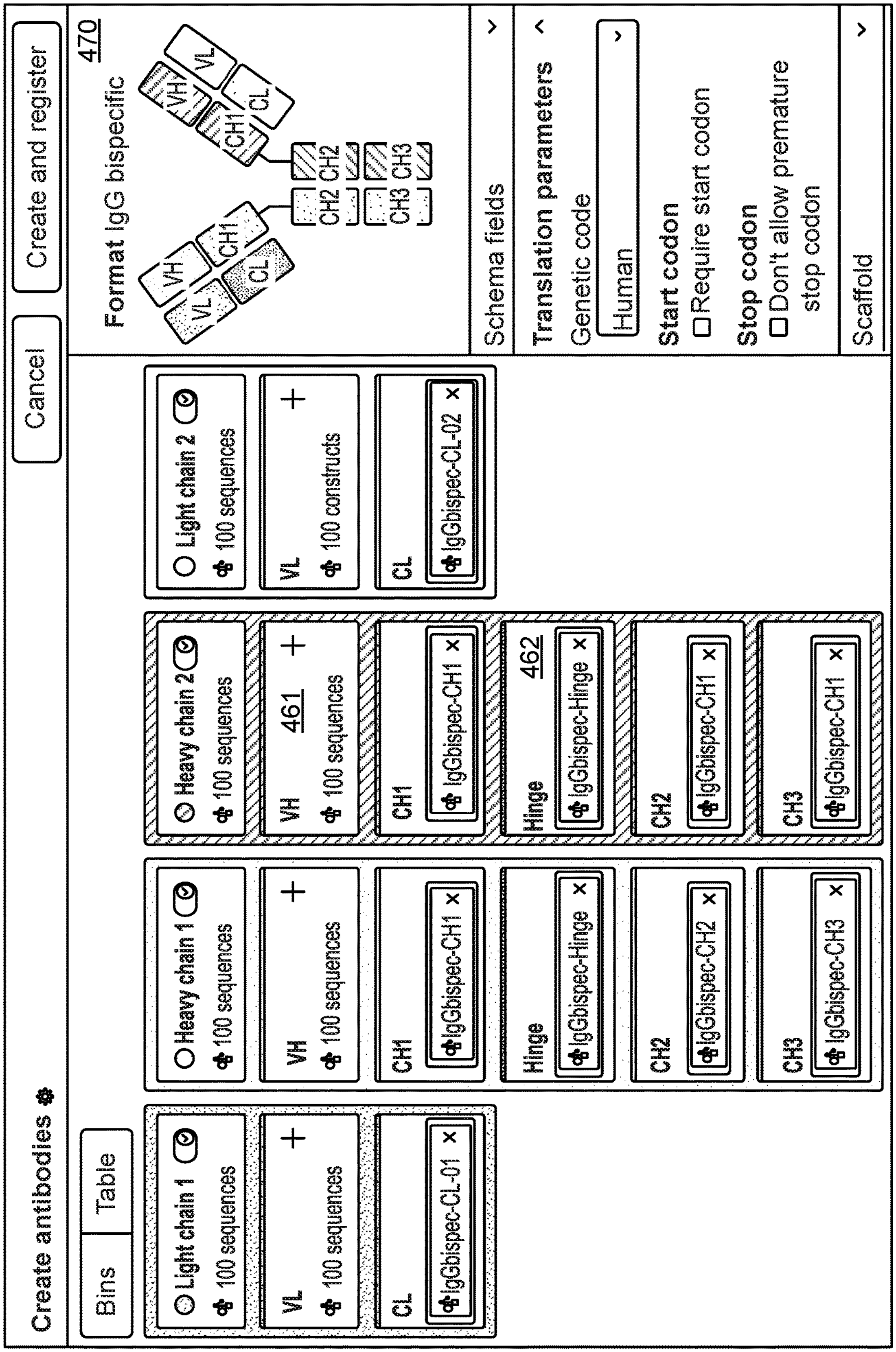
FIG. 4C shows an example user interface presentation.

FIG. 4C shows an example 450 user interface presentation.

In particular, example 450 is an example user interface displayed on a computer monitor to a user and executed through an electronic lab notebook and biological registry computer program, where a user can provide inputs to the user interface through the use of a mouse and keyboard connected to the computer.

Example 450 shows a data ingestion interface that enables users to input molecular entity data into the system for integration into a hierarchical representation of a protein complex. The interface is designed to support flexible and intuitive data entry workflows, allowing users to associate biological sequence data, such as DNA or amino acid sequences, with specific component slots of a selected format template.

The interface includes a structured layout that presents the component slots of the protein complex in a visual hierarchy. Each slot is labeled according to its structural role (e.g., VH, CH1, hinge, CH2, CH3), and users can interact with the interface to upload or select molecular entity data for each slot. For example, users may drag a sequence file into a designated slot, select a stored sequence from a dropdown menu, or enter sequence data manually.

In particular, FIG. 4C shows that the interface includes visual indicators that guide and inform the user's interaction with component slots. For example, plus icons, e.g., plus icon 461, within component slots (e.g., VH) signal that the user can add molecular entity data to those slots. Additionally, completed fields, such as "IgGbispecif-Hinge" 462 in the hinge component slot, indicate that a valid component has been assigned and validated for that slot. Toggles next to chain names allow users to expand or collapse nested components, facilitating intuitive navigation of the protein complex structure. The window 470 to the right includes the name of the format template "Format IgG bispecific" and a 2D visualization of the corresponding protein complex to inform the user of the type of protein complex the use is providing data for.

The system can validate the input data against the structural constraints defined in the format template, ensuring that the ingested data is biologically plausible and structurally consistent. Upon successful validation, the system populates the relational database with a record representing the component and links it to related components in the hierarchical model.

Importantly, the interfaces visualization of the format template enforces type and slot compatibility, preventing users from inadvertently mixing incompatible components, such as assigning a light chain sequence to a heavy chain slot. That is, each slot is governed by predefined structural rules defined by the corresponding format template that validate the biological role and entity type of the component, ensuring that only appropriate entities can be assigned. This constraint-driven design helps maintain biological fidelity and reduces the risk of modeling errors during data ingestion.

Figure 5:
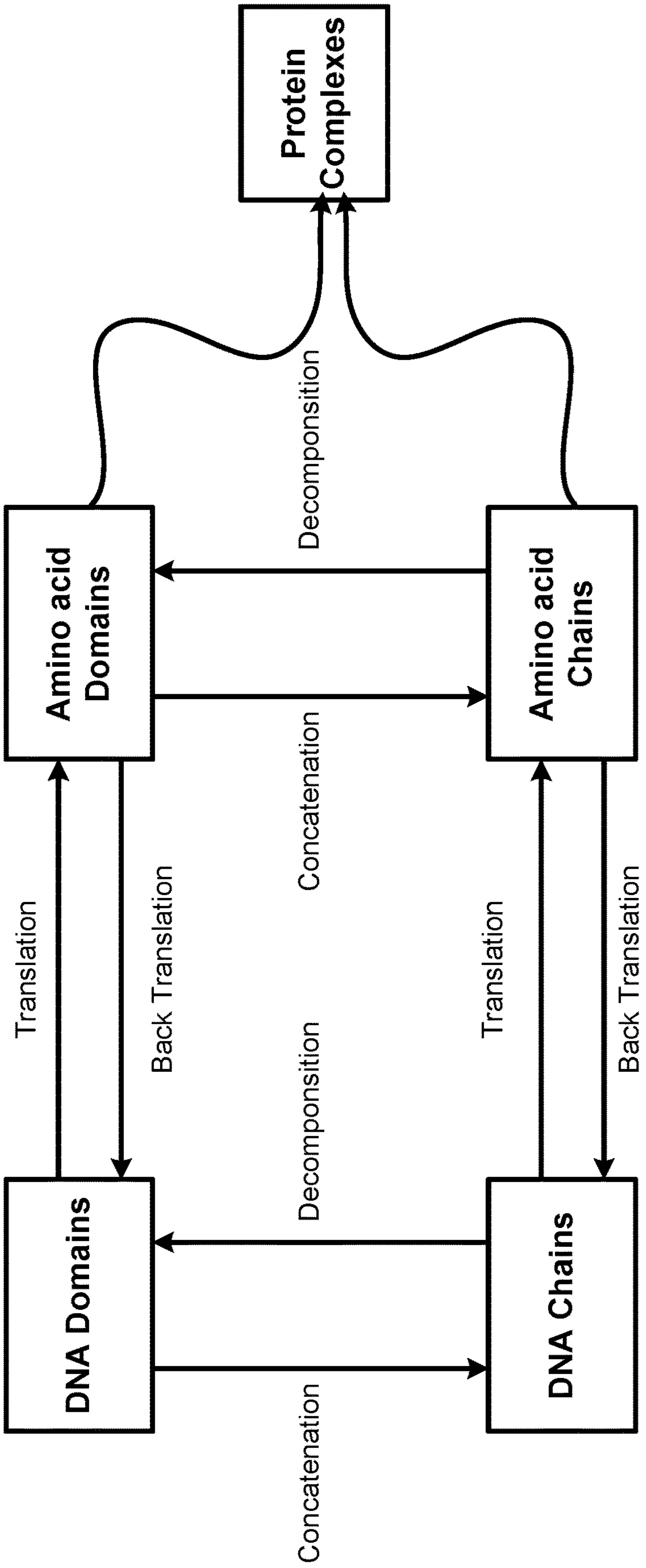
FIG. 5 shows a visual flow diagram of an example process for automatically generating component data according to one or more biological transformations.

FIG. 5 shows a visual flow diagram of an example process 500 for automatically generating component data according to one or more biological transformations.

The arrows in the diagram indicate the direction of transformation or inference between components and protein complexes, including processes such as concatenation, translation, back translation, and decomposition. These biological transformations enable the system to infer incomplete component data and maintain biologically coherent representations of protein complexes.

The diagram illustrates how data associated with components, e.g., such as DNA sequences and amino acid sequences, can be propagated across other components within a hierarchical representation. For example, when a DNA domain is provided, the system can automatically populate the corresponding DNA chain by "concatenating" domain-level sequences. Conversely, when a DNA chain is provided, the system can generate the underlying domain-level data by "decomposing" the DNA of the chain into domains. By autocompleting incomplete data, the system ensures that each component remains consistent with its parent and child components.

In addition to autocompleting incomplete data among parent and child components of a particular component, the system supports biological transformations between sequence types. For example, a DNA sequence can be translated into an amino acid sequence, and an amino acid sequence can be back translated into a corresponding DNA sequence. These transformations allow the system to fill in missing data across different biological representations, ensuring that when each component includes data representing a plurality of respective molecular entities that can serve as one or more portions of the protein complex, the related components are automatically populated and remain consistent with one another.

Following the generation and completion of component-level data, the system can, in some cases, further support the automated construction of full protein complexes. For example, amino acid domains and amino acid chains can be programmatically combined to form validated protein complexes. The system can enable various modes of combination, including exhaustive pairing of domain or chain variants. For example, given two user provided heavy chain variable domains and two user provided light chain variable domains, the system can generate all possible combinations, resulting in four distinct protein complexes. This combinatorial capability of the system allows users to rapidly explore diverse variations of protein complexes that have passed all in silico biological checks.

Thus, by applying these biological transformations, the system can automatically complete incomplete data in the hierarchical representation. This autocompletion is not only efficient but also self-consistent, meaning that inferred data aligns with the structural and biological constraints of the overall protein complex. As a result, users interacting with the system (e.g., by selecting a chain or domain on a user interface, e.g., FIG. 4) can access accurate, validated component data without manual verification.

The subject matter and the actions and operations described in this specification can be implemented in digital electronic circuitry, in tangibly-embodied computer software or firmware, in computer hardware, including the structures disclosed in this specification and their structural equivalents, or in combinations of one or more of them. The subject matter and the actions and operations described in this specification can be implemented as or in one or more computer programs, e.g., one or more modules of computer program instructions, encoded on a computer program carrier, for execution by, or to control the operation of, data processing apparatus. The carrier can be a tangible non-transitory computer storage medium. Alternatively, or in addition, the carrier can be an artificially generated propagated signal, e.g., a machine-generated electrical, optical, or electromagnetic signal, that is generated to encode information for transmission to suitable receiver apparatus for execution by a data processing apparatus. The computer storage medium can be or be part of a machine-readable storage device, a machine-readable storage substrate, a random or serial access memory device, or a combination of one or more of them. A computer storage medium is not a propagated signal.

The term "data processing apparatus" encompasses all kinds of apparatus, devices, and machines for processing data, including by way of example a programmable processor, a computer, or multiple processors or computers. Data processing apparatus can include special-purpose logic circuitry, e.g., an FPGA (field programmable gate array), an ASIC (application specific integrated circuit), or a GPU (graphics processing unit). The apparatus can also include, in addition to hardware, code that creates an execution environment for computer programs, e.g., code that constitutes processor firmware, a protocol stack, a database management system, an operating system, or a combination of one or more of them.

A computer program can be written in any form of programming language, including compiled or interpreted languages, or declarative or procedural languages; and it can be deployed in any form, including as a stand-alone program, e.g., as an app, or as a software module, component, engine, subroutine, or other unit suitable for executing in a computing environment, which environment may include one or more computers interconnected by a data communication network in one or more locations.

A computer program may, but need not, correspond to a file in a file system. A computer program can be stored in a portion of a file that holds other programs or data, e.g., one or more scripts stored in a markup language document, in a single file dedicated to the program in question, or in multiple coordinated files, e.g., files that store one or more modules, sub programs, or portions of code.

The processes and logic flows described in this specification can be performed by one or more computers executing one or more computer programs to perform operations by operating on input data and generating output. The processes and logic flows can also be performed by special-purpose logic circuitry, e.g., an FPGA, an ASIC, or a GPU, or by a combination of special-purpose logic circuitry and one or more programmed computers.

Computers suitable for the execution of a computer program can be based on general or special-purpose microprocessors or microcontrollers or a combination of them, or any other kind of central processing unit. Generally, a central processing unit will receive instructions and data from a read only memory or a random access memory or both. The essential elements of a computer are a central processing unit for executing instructions and one or more memory devices for storing instructions and data. The central processing unit and the memory can be supplemented by, or incorporated in, special-purpose logic circuitry.

Generally, a computer will also include, or be operatively coupled to, one or more mass storage devices, and be configured to receive data from or transfer data to the mass storage devices. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

To provide for interaction with a user, the subject matter described in this specification can be implemented on one or more computers having, or configured to communicate with, a display device, e.g., a LCD (liquid crystal display) monitor, or a virtual-reality (VR) or augmented-reality (AR) display, for displaying information to the user, and an input device by which the user can provide input to the computer, e.g., a keyboard and a pointing device, e.g., a mouse, a trackball or touchpad. Other kinds of devices can be used to provide for interaction with a user as well; for example, feedback and responses provided to the user can be any form of sensory feedback, e.g., visual, auditory, speech, or tactile feedback or responses; and input from the user can be received in any form, including acoustic, speech, tactile, or eye tracking input, including touch motion or gestures, or kinetic motion or gestures or orientation motion or gestures. In addition, a computer can interact with a user by sending documents to and receiving documents from a device that is used by the user; for example, by sending web pages to a web browser on a user's device in response to requests received from the web browser, or by interacting with an app running on a user device, e.g., on a smartphone or electronic tablet. Also, a computer can interact with a user by sending text messages or other forms of message to a personal device, e.g., a smartphone that is running a messaging application, and receiving responsive messages from the user in return.

This specification uses the term "configured to" in connection with systems, apparatus, and computer program components. That a system of one or more computers is configured to perform particular operations or actions means that the system has installed on it software, firmware, hardware, or a combination of them that in operation cause the system to perform the operations or actions. That one or more computer programs is configured to perform particular operations or actions means that the one or more programs include instructions that, when executed by data processing apparatus, cause the apparatus to perform the operations or actions. That special-purpose logic circuitry is configured to perform particular operations or actions means that the circuitry has electronic logic that performs the operations or actions.

The subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some implementations, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:

maintaining, in a relational database, a plurality of format templates, each format template defining a hierarchical representation of a protein complex, wherein each hierarchical representation of a protein complex has a plurality of component slots representing respective portions of the protein complex, wherein the database stores records for a plurality of components, each component comprising data representing a respective molecular entity that can serve as one or more portions of the protein complex, and wherein the database stores links representing parent and child relationships between components of the protein complex,
- wherein each format template defines one or more structure constraints between components of the protein complex;
- receiving user input specifying a component of a protein complex and a component slot of a format template; and
- populating the relational database with a record representing the component while enforcing the one or more structural constraints of the format template.

Embodiment 2 is the method of embodiment 1, wherein each component comprises data representing a plurality of respective molecular entities that can serve as one or more portions of the protein complex.

Embodiment 3 is the method of any one of embodiments 1-2, wherein the one or more structural constraints specify connection types that must be present or absent between components of the format template.

Embodiment 4 is the method of embodiment 3, wherein the connection types are based on molecular entity types of connected components of the protein complex.

Embodiment 5 is the method of any one of embodiments 1-4, wherein the one or more structural constraints specify which component types can or must not appear in component slots of the format template.

Embodiment 6 is the method of any one of embodiments 1-5, wherein the one or more structural constraints specify that only components corresponding to one symmetrical portion of the protein complex can be specified, and the system automatically generates a mirrored portion of the protein complex based on the specified symmetrical components.

Embodiment 7 is the method of any one of embodiments 1-6, further comprising:

generating a user interface that presents the hierarchical representation of the protein complex.

Embodiment 8 is the method of embodiment 7, wherein the user interface illustrates the component slots of the format template and identifies corresponding components stored in the database.

Embodiment 9 is a system comprising: one or more computers and one or more storage devices storing instructions that are operable, when executed by the one or more computers, to cause the one or more computers to perform the method of any one of embodiments 1 to 8.

Embodiment 10 is a computer storage medium encoded with a computer program, the program comprising instructions that are operable, when executed by data processing apparatus, to cause the data processing apparatus to perform the method of any one of embodiments 1 to 8.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A bioinformatics system comprising:

one or more computers and one or more storage devices storing instructions that are operable, when executed by the one or more computers, to cause the one or more computers to perform operations comprising:

maintaining, in a relational database, a plurality of format templates, each format template defining a hierarchical representation of a protein complex, wherein each hierarchical representation of a protein complex has a plurality of component slots representing respective portions of the protein complex, wherein the database stores records for a plurality of components, each component comprising data representing a respective molecular entity that can serve as one or more portions of the protein complex, and wherein the database stores links representing parent and child relationships between components of the protein complex, wherein each format template defines one or more structural constraints between components of the protein complex, wherein the one or more structural constraints specify connection types that must be present between components of the format template, the connection types defining a biological or chemical linkage between the components;

receiving user input specifying a component of a protein complex and a component slot of a format template; and populating the relational database with a record representing the component while enforcing the one or more structural constraints of the format template.

2. The system of claim 1, wherein each component comprises data representing a plurality of respective molecular entities that can serve as one or more portions of the protein complex.

3. The system of claim 1, wherein the one or more structural constraints specify connection types that must be absent between components of the format template.

4. The system of claim 3, wherein the connection types are based on molecular entity types of connected components of the protein complex.

5. The system of claim 1, wherein the one or more structural constraints specify which component types must appear in component slots of the format template.

6. The system of claim 1, wherein the one or more structural constraints specify that only components corresponding to one symmetrical portion of the protein complex can be specified, and the system automatically generates a mirrored portion of the protein complex based on the specified symmetrical components.

7. The system of claim 1, wherein the operations further comprise:

generating a user interface that presents the hierarchical representation of the protein complex.

8. The system of claim 7, wherein the user interface illustrates the component slots of the format template and identifies corresponding components stored in the database.

9. A method performed by one or more computers, the method comprising:

maintaining, in a relational database, a plurality of format templates, each format template defining a hierarchical representation of a protein complex, wherein each hierarchical representation of a protein complex has a plurality of component slots representing respective portions of the protein complex, wherein the database stores records for a plurality of components, each component comprising data representing a respective molecular entity that can serve as one or more portions of the protein complex, and wherein the database stores links representing parent and child relationships between components of the protein complex, wherein each format template defines one or more structural constraints between components of the protein complex, wherein the one or more structural constraints specify connection types that must be present between components of the format template, the connection types defining a biological or chemical linkage between the components;

receiving user input specifying a component of a protein complex and a component slot of a format template; and populating the relational database with a record representing the component while enforcing the one or more structural constraints of the format template.

10. The method of claim 9, wherein each component comprises data representing a plurality of respective molecular entities that can serve as one or more portions of the protein complex.

11. The method of claim 9, wherein the one or more structural constraints specify connection types that must be present between components of the format template.

12. The method of claim 11, wherein the connection types are based on molecular entity types of connected components of the protein complex.

13. The method of claim 9, wherein the one or more structural constraints specify which component types must appear in component slots of the format template.

14. The method of claim 9, wherein the one or more structural constraints specify that only components corresponding to one symmetrical portion of the protein complex can be specified, and the system automatically generates a mirrored portion of the protein complex based on the specified symmetrical components.

15. The method of claim 9, further comprising:

generating a user interface that presents the hierarchical representation of the protein complex.

16. The method of claim 15, wherein the user interface illustrates the component slots of the format template and identifies corresponding components stored in the database.

17. One or more non-transitory computer storage media storing instructions that when executed by one or more computers cause the one more computers to perform operations, the operations comprising:

maintaining, in a relational database, a plurality of format templates, each format template defining a hierarchical representation of a protein complex, wherein each hierarchical representation of a protein complex has a plurality of component slots representing respective portions of the protein complex, wherein the database stores records for a plurality of components, each component comprising data representing a respective molecular entity that can serve as one or more portions of the protein complex, and wherein the database stores links representing parent and child relationships between components of the protein complex, wherein each format template defines one or more structural constraints between components of the protein complex, wherein the one or more structural constraints specify connection types that must be present between components of the format template, the connection types defining a biological or chemical linkage between the components;

receiving user input specifying a component of a protein complex and a component slot of a format template; and populating the relational database with a record representing the component while enforcing the one or more structural constraints of the format template.

18. The one or more computer storage media of claim 17, wherein each component comprises data representing a plurality of respective molecular entities that can serve as one or more portions of the protein complex.

19. The one or more computer storage media of claim 17, wherein the one or more structural constraints specify connection types that must be absent between components of the format template.

20. The one or more computer storage media of claim 19, wherein the connection types are based on molecular entity types of connected components of the protein complex.

* * * * *